(12) United States Patent
Rosengaus

(10) Patent No.: US 7,176,433 B1
(45) Date of Patent: Feb. 13, 2007

(54) RESOLUTION ENHANCEMENT FOR MACRO WAFER INSPECTION

(75) Inventor: Eliezer Rosengaus, Palo Alto, CA (US)

(73) Assignee: KLA-Teacor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/992,244

(22) Filed: Nov. 17, 2004

Related U.S. Application Data

(60) Provisional application No. 60/569,092, filed on May 7, 2004.

(51) Int. Cl.
- *H01L 27/00* (2006.01)
- *G01N 21/00* (2006.01)
- *G01N 21/88* (2006.01)
- *G01N 21/84* (2006.01)

(52) U.S. Cl. .............. 250/208.1; 250/559.05; 250/559.06; 250/559.07; 250/559.4; 356/431; 356/237.4; 356/237.5

(58) Field of Classification Search .......... 250/208.1, 250/216, 559.04–559.08, 559.4–559.49; 356/429–431, 237.2–237.5; 702/35, 40; 382/144, 145, 148, 149

See application file for complete search history.

(56) References Cited

U.S. PATENT DOCUMENTS

| | | | |
|---|---|---|---|
| 5,917,588 A | 6/1999 | Addiego | 356/237 |
| 6,724,489 B2 * | 4/2004 | Freifeld | 356/601 |
| 6,765,651 B1 * | 7/2004 | Fiekowsky et al. | 355/77 |
| 6,879,403 B2 * | 4/2005 | Freifeld | 356/601 |
| 6,911,639 B2 * | 6/2005 | Boemler et al. | 250/208.1 |
| 2004/0032581 A1 * | 2/2004 | Nikoonahad et al. | 356/237.2 |
| 2004/0096118 A1 * | 5/2004 | Liang | 382/284 |
| 2004/0101210 A1 * | 5/2004 | Weinstein et al. | 382/284 |
| 2005/0146714 A1 * | 7/2005 | Kitamura et al. | 356/237.2 |

* cited by examiner

*Primary Examiner*—Stephone B. Allen
*Assistant Examiner*—Davienne Monbleau
(74) *Attorney, Agent, or Firm*—Deborah W. Wenocur

(57) ABSTRACT

A method and apparatus for improving system resolution for a defect line scanner while not increasing aliasing effects, or alternatively to maintain system resolution for a defect scanner while decreasing aliasing effects. This is accomplished by decreasing effective pixel size for a CCD array defect line scanner while not decreasing signal-to-noise ratio, with minimal changes to the current machine. The method utilizes a sampling phase shift between successive lines of a multi-line sensor array during scanning.

19 Claims, 5 Drawing Sheets

RESOLUTION ENHANCEMENT FOR MACRO WAFER INSPECTION

CROSS REFERENCE TO RELATED APPLICATION

This application claims priority from U.S. Provisional Application No. 60/569,092, filed on May 7, 2004.

FIELD OF THE INVENTION

This invention relates to defect detection on integrated circuit wafers, and in particular to a method of achieving reduced effective pixel size for a wafer inspection system, thereby improving resolution.

BACKGROUND OF THE INVENTION

As integrated circuit device densities continue to increase and correspondingly device and circuit dimensions continue to decrease, wafer inspection systems for macro-defect detection, primarily used in the lithography steps of wafer manufacture, must move to higher resolution. This will preferably be accomplished while maintaining the extremely high throughput achieved by currently available inspection systems. By way of example, the KLA-Tencor 2430 inspection system is a 300-mm capable inspector, with a throughput of up to 100 to 140 wafers per hour. Since at present, most macroscopic defects of interest are in the 30 micron and above size range, the 2430 is designed to have a pixel size of 39 microns, which achieves 30 to 50 micron defect detection, depending on the defect type and the background. However, with the downward evolution of device dimensions, there is currently strong interest in increasing the resolution of the system so as to detect defects in the 10 micron size range, while maintaining the throughput of the current system.

Microarray scanners produce images composed of a matrix of pixels, where each represents the intensity of light emanating from a small illuminated area of the sample. The scanner for detection systems such as the KLA-Tencor 2430 system is a CCD scanner with the sample illumination being line illumination using a source such as shaped fiber optics from a lamp. It is comprised of an array of sensors, each of which is a photodiode which produces electron-hole pairs when a photon is incident, thereby causing a charge build-up. Adjacent photo-diode sensors are separated by isolation such as trench isolation. FIG. 1 illustrates incident light 100 impinging on sample 110, with outgoing light from the sample (which may be reflected, scattered, or diffracted light) passing through optical elements 120 to sensor array 130 comprising sensors 140.

System resolution is derived from both pixel resolution and optical resolution. The pitch of the detector elements or sensors determines pixel resolution, since each pixel integrates the incoming signal over its area. Optical resolution is determined by the performance of optical elements 120. It is possible to increase system resolution, i.e., to resolve smaller defects on the sample surface, by several methods, including: 1) the pixel size may be held constant, but a larger sensor array containing more pixels (sensors) may be used, with the optical elements acting to spread the outgoing light from the sample onto the larger array area, or 2) the sensor array may be held at a constant size, but the number of pixels may be increased by decreasing the sensor size and pitch. Each of these methods has drawbacks:

1) The size of the sensor array is limited mainly by photolithography considerations. The yield of the sensor array is considerably higher if it is fabricated in a single lithography step, which for current processing methods limits the array size to about 75 mm.

2) A lower limit to pixel size is imposed by an effect known as Schott noise, which is the variation in charge build-up in a sensor for each sampling time. The Schott noise is proportional to the square root of the number of electrons, whereas the photodiode signal is proportional to the number of electrons. Therefore, the signal-to-noise ratio decreases as the number of electrons decreases. This effect is unavoidable and is a consequence of the Poisson statistics that govern electrons. The well capacity of a photodiode sensor (maximum number of electrons stored therein) is determined by the capacitance of the photodiode, which is in turn proportional to the area of the photosensor. By way of example, the present sensor element used in the KLA-Tencor 2430 system is of nine square micron size, and has a capacity of about 400 K electrons per well. A next generation sensor of 7 square micron size has a capacity of about 250 K electrons per well, with correspondingly greater (percentually) Schott noise. Accordingly, the greater resolution afforded by decreasing pixel size is accompanied by poorer signal to noise ratio. Averaging over repeated measurements can reduce Schott noise, but this technique lowers throughput.

An important improvement for defect detection systems would be a reduction in effective pixel size, or alternatively an increase in the effective number of pixels per unit area of the sensor array, while avoiding increased Schott noise. In either case, this would allow better sampling of the sample surface, to see higher frequency effects such as smaller defect sizes, and also to avoid aliasing. For example, according to the Nyquist theorem, in order to reconstruct a real signal for a feature without getting an aliasing effect, at least two samplings are required across the feature; i.e., the sampling frequency must be at least double the feature frequency. Descriptions of aliasing and related effects can be found in: *Digital Image processing and Computer Vision*, Robert J. Schalkoff, John Wiley and Sons, 1989, pp 112 ff, and in *Digital Image Processing*, Rafael C. Gonzalez and Richard E. Woods, Addison Wesley, 1992, pp 112ff.

SUMMARY OF THE INVENTION

It is therefore an object of this invention to provide a method for improving system resolution for a defect line scanner while not increasing aliasing effects, or alternatively to maintain system resolution for a defect scanner while decreasing aliasing effects.

It is a further object of this invention to provide a method for decreasing effective pixel size for a CCD array defect line scanner while not decreasing signal-to-noise ratio.

It is a further object of this invention to provide a method for decreasing effective pixel size for a CCD array defect line scanner while not decreasing signal-to-noise ratio, with minimal changes to the current machine.

These objects are met in one embodiment by a simple modification to the geometry of a multiple line scanner sensor array.

These objects are met in another embodiment by modifications to the configuration of a multiple line scanner sensor array.

DETAILED DESCRIPTION OF THE INVENTION

Figure 1:
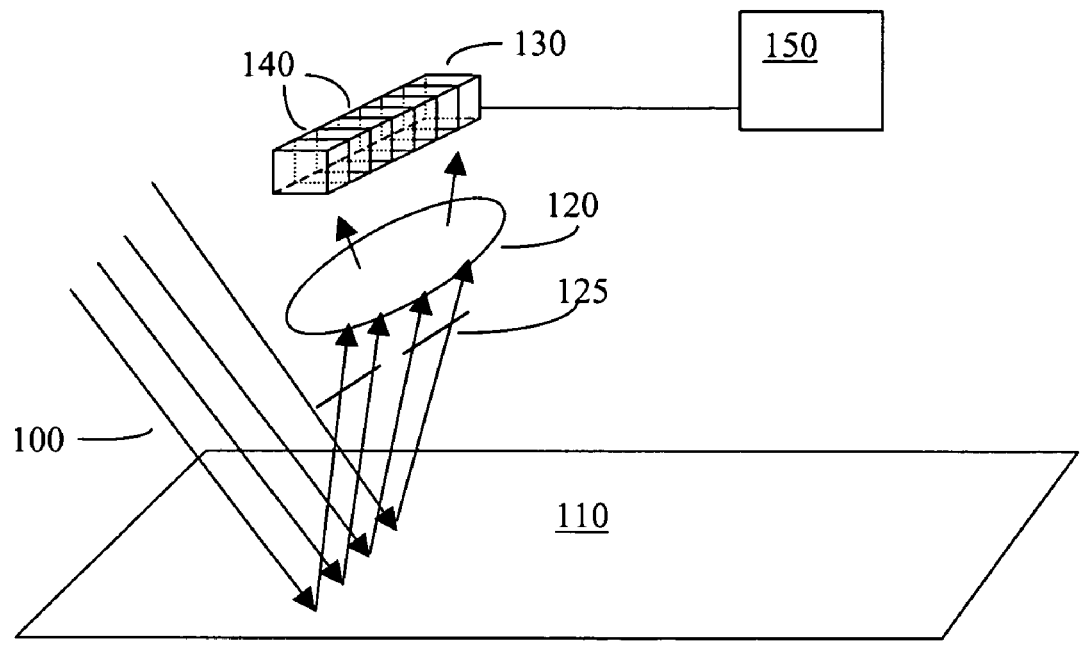
FIG. 1 illustrates the CCD sensor array in relation to the sample and incoming and outgoing light.
Figure 2A:
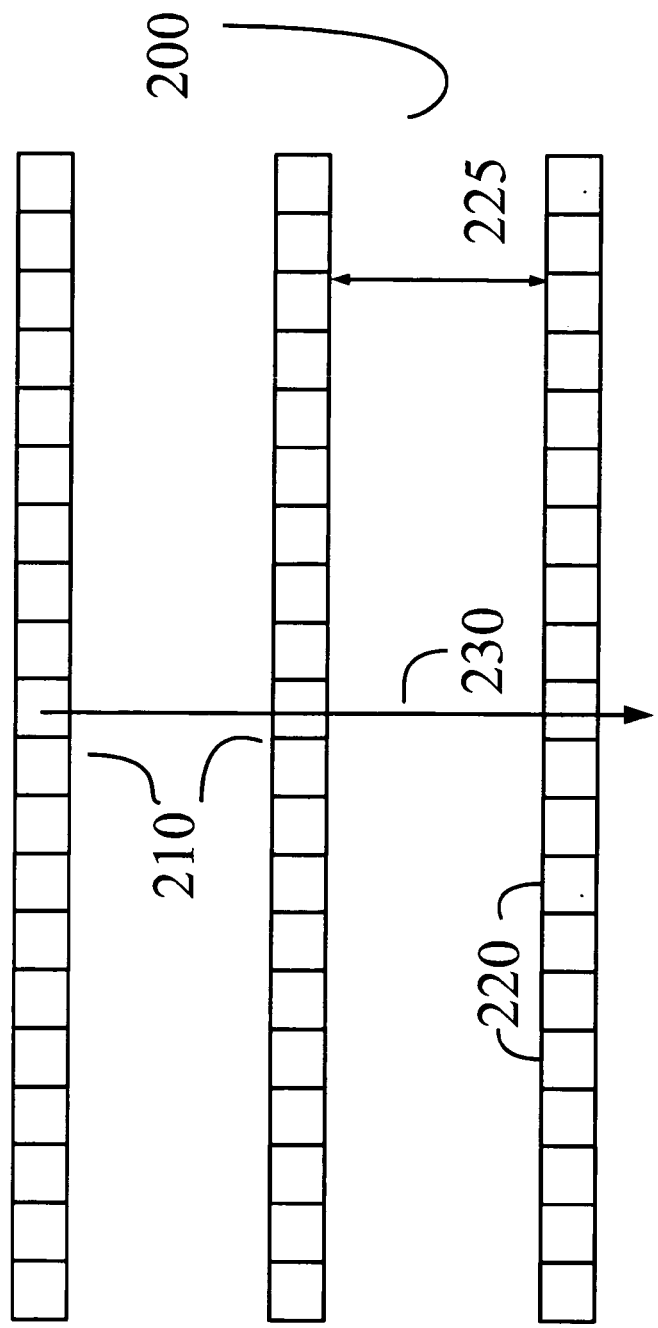
FIG. 2a illustrates the sensor array in the current implementation.

A scanner currently used in a KLA-Tencor line-scan macro-inspection system utilizes a CCD sensor array comprised of an 8000 pixel wide array of sensor elements, to image the full width of the wafer in a single pass. (It should be noted that the details of the system as described herein, e.g., the number of lines in the sensor array, and the spacing therebetween, are exemplary and not limiting). This is a tri-linear sensor array designed for use in document scanning. FIG. 2a illustrates the sensor array in the current implementation. Sensor array 200 comprises three parallel and coplanar lines (also called "linear arrays" or "channels") 210 containing sensor elements 220, each element of which is the photosensitive area of a pixel. Linear arrays 210 are separated by distance 225, which is 12 pixels high in the current implementation. The space between the linear arrays is utilized for read-out circuitry. In document scanning, each of the three channels is covered with an absorption polyimide filter to select one of red, green, and blue bands for each of the three lines. In the current implementation, the sensor manufacturer does not apply the color filters. The scanner system operates either by reading one of the three lines, or alternatively by reading all three lines and adding the signals for noise reduction, after correcting for the displacement between lines. At present, the sensor array is scanned across the sample in the direction of arrow 230 (hereinafter described as vertical), i.e., perpendicular to the orientation of linear arrays 210 (which in this implementation is horizontal). The pixels on each of the three lines are aligned horizontally: accordingly, as the scan object is scanned in the scan direction 230, each line 210 samples the scan object in the same horizontal position. This is redundant sampling when, as in the current implementation, the color information is not used. The data from each channel can be read independently and transferred to computer memory after digitization.

Scanning of integrated circuit wafers is complicated by such factors as:

1) The high intrinsic periodicity of integrated circuits as well as the large incidence of very high spatial frequency features, both in terms of size and of sharply delineated features. Both of these aspects cause scanning of integrated circuit wafers to be highly subject to aliasing effects, e.g., in comparison with document scanning 2) The mirror finish of most integrated circuit wafers, joined with diffractive effects, can make the wafers very efficient in diverting light away from the capture cone of the collecting optics; this can impose heavy requirements on the intensity and angular distribution of the illumination (particularly in darkfield configurations).

The present invention provides a method and apparatus for wafer scanning in a macro-defect detection system, which yield an increase in the effective number of pixels in a multi-line sensor array (and thereby the capability of imaging higher frequency features without increasing aliasing), without increased Schott noise. In order to achieve this, the actual area encompassed by each photodiode is maintained, so as to maintain the electron capacity of the wells.

According to a first embodiment of the method of the present invention, the effective pixel resolution is improved by utilizing a sampling phase shift between successive lines of a multi-line sensor array during scanning. Corresponding pixels in successive lines are offset by a portion of a pixel. Although each pixel is still integrating the signal across its full width, the information content of corresponding pixels in each channel is now different. By numerical deconvolution, the sampling can be reconstructed as though the sampling had been done with a single channel containing a larger number of pixels. Discussions of applicable numerical deconvolution techniques are found in:

Lucy, L. B., *Astron. Journal* 79, pp 745 (1974), Richardson, W. H., *J. Opt. Soc. Am.*, 62, pp 55 (1972), and *Digital, mage Processing*, Rafel C. Gonzalez and Richard E. Woods, Addison Wesley, 1992, pp 195 ff.

Figure 2B:
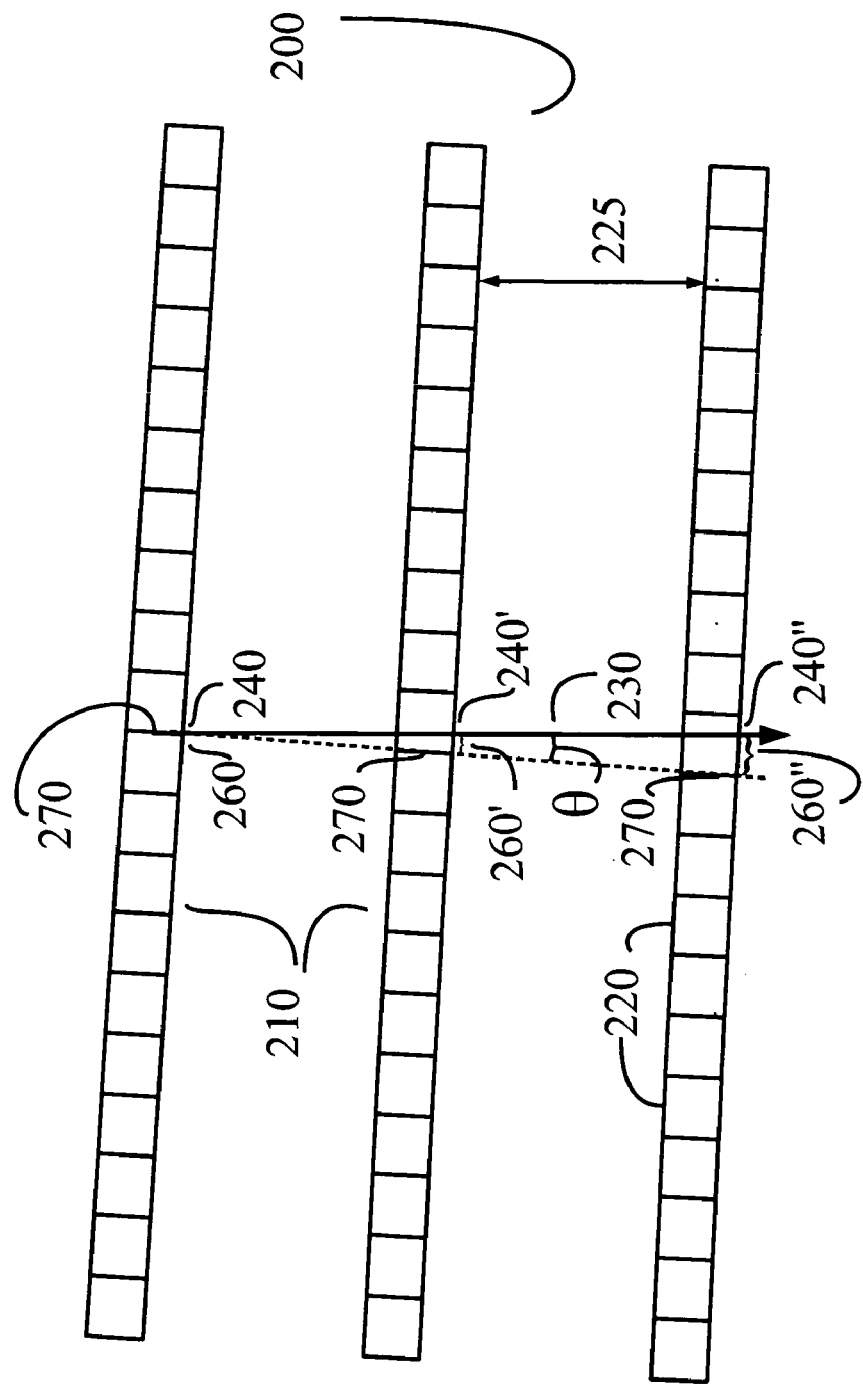
FIG. 2b illustrates a sensor array rotated in the focal plane by an angle θ with respect to the scan direction.

A preferred method of achieving this phase shift is accomplished with a simple modification to the geometry of the sensor array. An example of this modified geometry, corresponding to the tri-linear sensor array of FIG. 2a, is illustrated in FIG. 2b. The sensor array is rotated in the focal plane by an angle θ with respect to the scan direction 230. In this configuration, as the object is scanned, it is sampled at different locations by each of the three channels. If the rotation angle θ is chosen to have a tangent of ⅟36, corresponding to approximately 1.6 degrees, the sampling of each channel will shift by exactly ⅓ pixel between adjacent channels. This is illustrated in FIG. 2b in which points 240, 240' and 240" intersect center line 250 at distances 260, 260', and 260" from pixel edges 270. Distance 260' (corresponding to the shift in sampling position between adjacent channels) divided by separation distance 225 equals tan θ. Therefore, if separation distance 225 is 12 pixels, then the shift is ⅓ pixel, and the sampling can be reconstructed as though the sampling had been done with a single channel containing three times as many pixels. It should be noted that the number of sensor lines used, and the angular rotation amount, can be varied.

A benefit of the aforementioned embodiment, in addition to the improved effective pixel density, is its simplicity. No custom components are needed, and costs are low since off the shelf components may be used. No hardware modifications are required, only software and build/align procedures which produce the actual tilting of the array. Another benefit of the embodiment is that the changing of the sampling phase reduces aliasing effects, since more effective samples per unit distance along the channel are taken, and high frequency effects are averaged out. The high frequency content of the image can be further controlled with a lens 120 between the sample and the sensor array, e.g. by stopping the lens with an aperture 125, which can decrease aliasing by low-passing, though at the price of reduced resolution. Additionally, this embodiment makes maximum use of the photosensitive surface and therefore has minimum illumination intensity requirements. Alternatively, the lens aperture can be increased while maintaining the aliasing noise levels of a single-line configuration (due to the finer sampling achieved), and increasing the light-collection efficiency of the system; this allows for higher throughput with equivalent illumination sources.

Figure 2C:
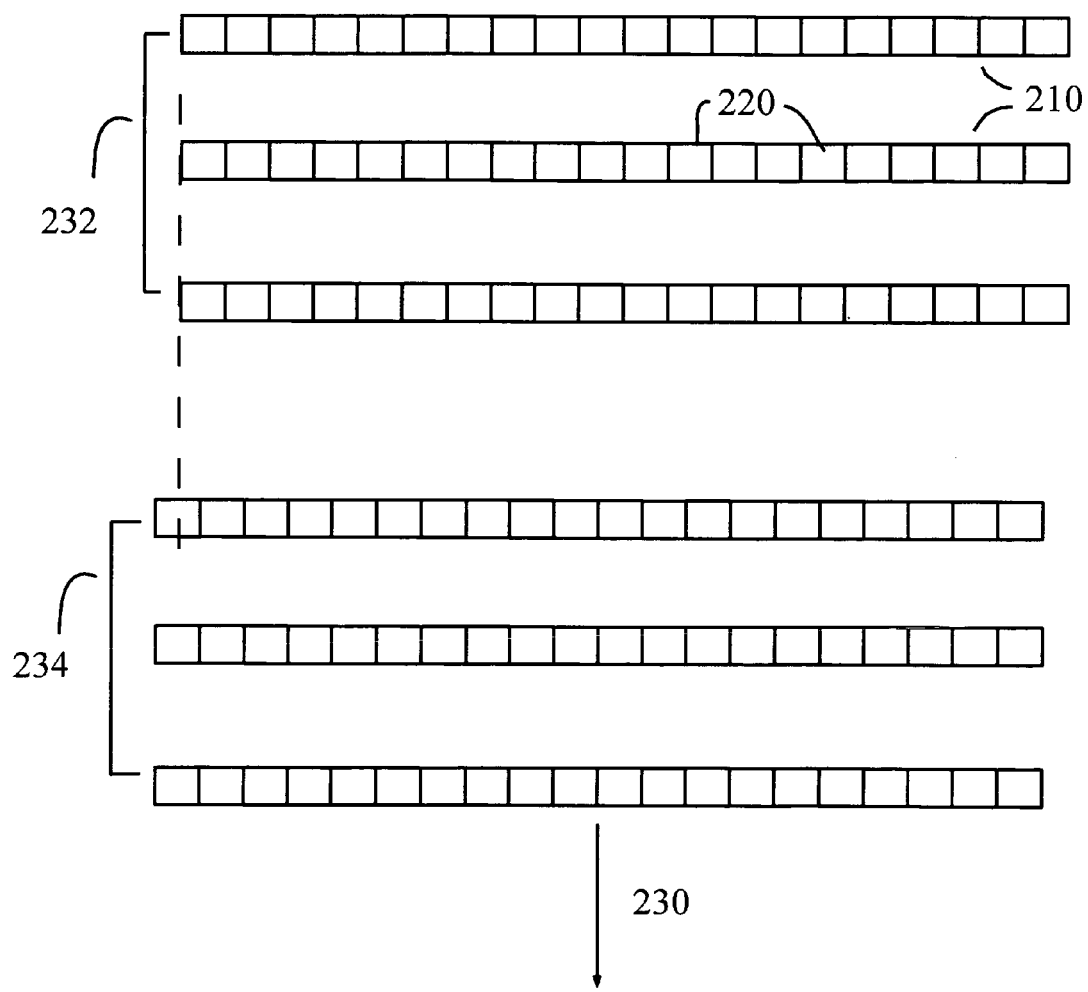
FIG. 2c illustrates a sensor array having two sets 232 and 234 of three linear arrays, being horizontally displaced from one another by ½ pixel.

An alternative sub-embodiment, illustrated in FIG. 2c, uses a modified multi-line sensor array to produce the offset in successive pixels. This method utilizes a sensor array having multiple sets 232 and 234 of linear arrays, two sets each having three linear arrays in the example illustrated, being horizontally displaced from one another by a fraction of a pixel, by way of example ½ pixel as illustrated. The overlapping signals, when deconvolved, yield an effective increase in pixel density (a factor of two in the illustrated example). This method does require the use of custom-made sensor arrays, but it enables alignment with perpendicularity (which is easier for manufacture than a precise small angle rotation). This method can be generalized to having n linear arrays or linear array sets, each being progressively horizontally displaced relative to the adjacent array or array set by 1/n pixel, resulting in an increase in effective pixel density by a factor of n. A custom sensor having 2 or 3 linear sensor arrays progressively offset by ½ or ⅓ pixel respectively, would be an effective implementation of this sub-embodiment.

Figure 3:
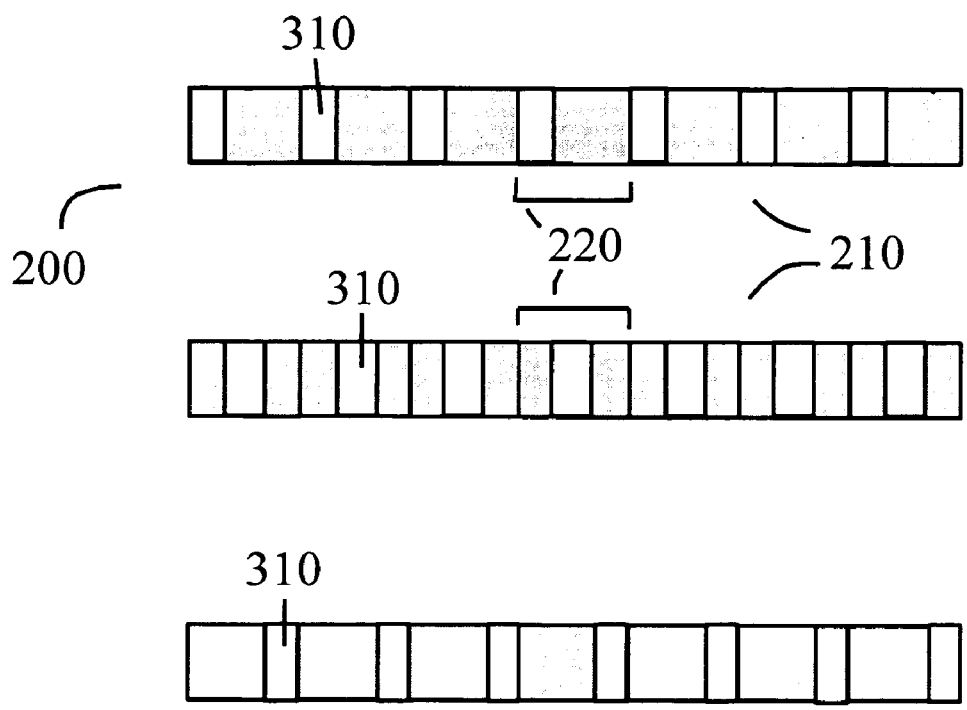
FIG. 3 illustrates a sensor array having successive portions of pixels masked.

In a second embodiment of the invention, illustrated in FIG. 3, effective pixel density increase is achieved by masking portions of each sensor: the sensor manufacturer deposits an opaque mask over each channel, wherein only a fraction of each pixel is left unmasked (in the example shown, ⅓ of each pixel is left unmasked). The unmasked portion 310 is shifted in each successive channel, such that the sampling is performed at progressively offset locations. Using this method, a true (3× in the illustrated example) effective pixel density increase is achieved, and horizontal resolution is improved, without the necessity of deconvolving overlapping signals. Well capacity remains the same for each sensor and therefore Schott noise is not increased, even though the exposed photosensitive surface area is decreased. However, increased illumination intensity is required, and custom modifications are needed to the sensor array. Resolution in the direction of the scan can be improved by reading more lines with a smaller displacement therebetween.

System Considerations

The present invention can be implemented, as an example, for macro defect detection on integrated circuit wafers, with no substantial hardware modifications to the present wafer scanning systems such as the KLA-Tencor 2401, which is utilized for wafers up to 200 mm diameter, or the KLA-Tencor 2430, which is utilized for wafers up to 300 mm diameter. Aspects of these systems are described in U.S. Pat. No. 5,917,588 by Addiego et al, which is hereby incorporated by reference. In one embodiment of the present invention, the scanning sensor array must be rotated by a precisely determined amount. The computing system 150 must be configured to process a much larger amount of data than with the unmodified sensor array, nine times more data for the embodiment described herein where each of three sensor lines is provided with an effective three times increase in pixel density.

The inventive modifications to the currently used scanning sensor array for a macro wafer inspection system such as the KLA-Tencor 2401 or 2430 models are very easily implemented, and yield substantial improvement in imaging of high frequency features, as well as reduction in aliasing effects and maintaining of signal-to-noise ratio. It is not intended that the invention be restricted to the exact embodiments described: it will be apparent to one skilled in the art that changes may be made without departing from the inventive concept. By way of example, scanning of the wafer can be accomplished by moving the scanner sensor array across the wafer, or alternatively by moving the wafer relative to the scanner sensor array: any method of causing relative motion between the wafer and the scanner sensor array may be used. As a second example, imaging systems other than standard lens imaging systems may be used, such as: fiber optics or contact image sensors (i.e., gradient index lenses). Gradient index lenses are described in *MicroOptics Technology; Fabrication and Application of Lens Arrays and Devices*, Nicholas F. Borrelli, Marcel Dekker Inc., 1999, Chapters 3 and 5. As a third example, the method can be applied to micro-inspection systems, with optical elements 120 providing magnification. As another example, standard color filters may be added to each channel, though this would complicate deconvolution of the signals. The exact rotation angle and channel configuration may be varied, as well as the exact elements of the data deconvolution system. The scope of the invention should be construed in view of the claims.

With this in mind, I claim:

1. A line-scan wafer inspection system having the capability of forming an image of an illuminated wafer sample, said wafer inspection system including:
   a line imaging system and associated optics;
   said imaging system including a scanner sensor array for optically sampling outgoing light from said sample surface, said scanner sensor array comprising a plurality of coplanar linear sensor arrays in a focal plane, each said linear sensor array arranged perpendicular to a scan direction of said scanner sensor array relative to said sample, each said linear sensor array comprising abutting optical sensors, each said sensor being a pixel having a pixel width, each said linear sensor array having an actual linear pixel density, wherein;
   said scanner sensor array is arranged to provide a shift in sampling in adjacent linear sensor arrays, wherein the sampling in at least a portion of said linear sensor arrays is shifted by a fraction of a pixel width with respect to adjacent linear sensor arrays, to provide optical sampling data from said sample which yields an effective linear pixel density greater than said actual linear pixel density;
   wherein said shift in sampling in adjacent linear sensor arrays is provided by one selected from the group consisting of:
   a) said scanner sensor array being rotated in said focal plane by an angle θ with respect to said scan direction; and
   b) a first portion of each pixel being masked and a second portion of each pixel being unmasked, wherein said second portion is shifted in each successive linear sensor array, such that the sampling is performed at progressively offset locations.

2. The wafer inspection system of claim 1, wherein said associated optics includes a lens between said sample and said sample sensor array.

3. The wafer inspection system of claim 2, further including an aperture for stopping said lens.

4. The wafer inspection system of claim 1, wherein said associated optics provide magnification to provide for micro-inspection.

5. The wafer inspection system of claim 1, wherein said imaging system includes non-standard elements.

6. The wafer inspection system of claim 1, wherein said imaging system includes gradient index lenses.

7. The wafer inspection system of claim 1, wherein said sampling in at least a portion of adjacent linear sensor arrays is partially overlapping in corresponding pixels of said adjacent linear sensor arrays, such that said effective linear pixel density greater than said actual linear pixel density is provided by deconvolving data from said partially overlapping sampling.

8. The wafer inspection system of claim 7, further including a computer system configured to process said data from said partially overlapping sampling so as to deconvolve said data.

9. The wafer inspection system of claim 1, wherein said scanner sensor array is rotated in said focal plane by an angle $\theta$ with respect to said scan direction to provide said shift in sampling in adjacent linear sensor arrays.

10. The wafer inspection system of claim 9, wherein said scanner sensor array comprises n linear sensor arrays, and wherein said angle $\theta$ with respect to said scan direction is chosen such that said shift in sampling in adjacent linear sensor arrays is 1/n pixels.

11. The wafer inspection system of claim 10, wherein n=3.

12. The method of claim 10, wherein said angle $\theta$ is no larger than on the order of 1.6 degrees.

13. The wafer inspection system of claim 1, where a first portion of each pixel is masked and a second portion of each pixel is unmasked, wherein said second portion is shifted in each successive linear sensor array, such that the sampling is performed at progressively offset locations to provide said shift in sampling in adjacent linear sensor arrays.

14. The wafer inspection system of claim 13, wherein said scanner sensor array comprises n linear sensor arrays, and wherein said shift of said second portion in each successive linear sensor array is 1/n pixels.

15. A method for increasing effective pixel resolution in a line-scan wafer inspection system including a scanner sensor array comprising a plurality of coplanar linear sensor arrays in a focal plane, each said linear sensor array comprising abutting sensors, each said sensor being a pixel having a pixel width, the method comprising:
  providing said scanner sensor array, arranged to sample outgoing light from the surface of said wafer sample, such that the sampling in at least a portion of adjacent linear sensor arrays is shifted by a fraction of a pixel;
  providing a wafer sample to be imaged;
  providing a line imaging system and associated optics;
  causing relative motion in a scan direction between said scanner sensor array and said wafer sample, said wafer sample being illuminated;
  sampling outgoing light from said wafer sample with said scanner sensor array, each said sensor of one pixel width yielding an electrical signal; and
  processing said electrical signals from said sensors of one pixel width to form an image of said wafers;
  wherein the step of providing said scanner sensor array arranged to sample outgoing light from the surface of said wafer sample such that the sampling in at least a portion of adjacent linear sensor arrays is shifted by a fraction of a pixel is performed by one of the group consisting of:
  a) arranging said scanner sensor array to be rotated in said focal plane by an angle $\theta$ such that said coplanar linear sensor arrays are arranged at said angle $\theta$ with respect to the perpendicular to the scan direction; and
  b) arranging said scanner sensor array such that a first portion of each pixel is masked and a second portion of each pixel is unmasked, wherein said second portion is shifted in each successive linear sensor array, such that the sampling is performed at progressively offset locations.

16. The method of claim 15, further including the step of deconvolving overlapping sampling data from corresponding pixels in adjacent linear sensor arrays.

17. The method of claim 15, wherein the step of providing said scanner sensor array arranged to sample outgoing light from the surface of said wafer sample such that the sampling in at least a portion of adjacent linear sensor arrays is shifted by a fraction of a pixel includes arranging said scanner sensor array to be rotated in said focal plane by an angle $\theta$ such that said coplanar linear sensor arrays are arranged at said angle $\theta$ with respect to the perpendicular to the scan direction.

18. The method of claim 17, wherein said angle $\theta$ is no larger than on the order of 1.6 degrees.

19. The method of claim 15, wherein the step of providing said scanner sensor array, arranged to sample outgoing light from the surface of said wafer sample, such that the sampling in at least a portion of adjacent linear sensor arrays is shifted by a fraction of a pixel includes arranging said scanner sensor array such that a first portion of each pixel is masked and a second portion of each pixel is unmasked, wherein said second portion is shifted in each successive linear sensor array, such that the sampling is performed at progressively offset locations.

* * * * *